US012000841B2

United States Patent
Chen et al.

(10) Patent No.: US 12,000,841 B2
(45) Date of Patent: Jun. 4, 2024

(54) DIAGNOSTIC KITS AND METHODS CONFIGURED TO RAPIDLY AND NON-INVASIVELY DETERMINE PHYSIOLOGIC LEVELS OF GALACTOSE-DEFICIENT IgA1 (Gd-IgA1) IN THE SUBJECT OF IgA NEPHROPATHY

(71) Applicants: National Defense Medical Center, Taipei (TW); Academia Sinica, Taipei (TW)

(72) Inventors: Ann Chen, Taipei (TW); Shuk-Man Ka, Taipei (TW); Shih-Hsiung Wu, Taipei (TW)

(73) Assignee: NATIONAL DEFENSE MEDICAL CENTER & ACADEMIA SINICA, Taipei (TW)

( * ) Notice: Subject to any disclaimer, the term of this patent is extended or adjusted under 35 U.S.C. 154(b) by 828 days.

(21) Appl. No.: 17/084,125

(22) Filed: Oct. 29, 2020

(65) Prior Publication Data
US 2021/0123927 A1    Apr. 29, 2021

Related U.S. Application Data

(60) Provisional application No. 62/927,281, filed on Oct. 29, 2019.

(51) Int. Cl.
G01N 33/68    (2006.01)
C07K 14/705   (2006.01)

(52) U.S. Cl.
CPC ..... *G01N 33/6854* (2013.01); *C07K 14/7056* (2013.01); *C12Q 2537/125* (2013.01); *G01N 2800/347* (2013.01)

(58) Field of Classification Search
CPC .......... C07K 14/7056; C12Q 2537/125; G01N 33/6854; G01N 2800/347
See application file for complete search history.

(56) References Cited

PUBLICATIONS

Jakób et al. (Acta Cryst., 2015, F71, 1429-1436) (Year: 2015).*
Chikalovets et al. (Fish & Shellfish Immunology, 2016, 50:27-33) (Year: 2016).*

* cited by examiner

*Primary Examiner* — Jeremy C Flinders
(74) *Attorney, Agent, or Firm* — Muncy, Geissler, Olds & Lowe, P.C

(57) ABSTRACT

The present invention provides a lectin from *Crenomytilus grayanus* or *Mytilus trossulus* as diagnostic reagents for IgA nephropathy. The present invention also provides a diagnostic kit for detecting Galactose-deficient IgA1 (Gd-IgA1), comprising RussiaSea-001 (also called as CGL) isolated from *Crenomytilus grayanus* or RussiaSea-002 (also called as MTL) isolated from *Mytilus trossulus*. The present invention further provides a method for detecting Gd-IgA1 using RussiaSea-001 or RussiaSea-002.

6 Claims, 11 Drawing Sheets
Specification includes a Sequence Listing.

SEQUENCE LISTING

```
<160> NUMBER OF SEQ ID NOS: 2

<210> SEQ ID NO 1
<211> LENGTH: 158
<212> TYPE: PRT
<213> ORGANISM: Artificial Sequence
<220> FEATURE:
<223> OTHER INFORMATION: RussiaSea-001

<400> SEQUENCE: 1

Met Thr Thr Phe Leu Ile Lys His Lys Ala Ser Gly Lys Phe Leu His
1               5                   10                  15

Pro Tyr Gly Gly Ser Ser Asn Pro Ala Asn Asn Thr Lys Leu Val Leu
            20                  25                  30

His Ser Asp Ile His Glu Arg Met Tyr Phe Gln Phe Asp Val Val Asp
        35                  40                  45

Glu Arg Trp Gly Tyr Ile Lys His Val Ala Ser Gly Lys Ile Val His
    50                  55                  60

Pro Tyr Gly Gly Gln Ala Asn Pro Pro Asn Glu Thr Asn Met Val Leu
65                  70                  75                  80
```

-continued

```
His Gln Asp Arg His Asp Arg Ala Leu Phe Ala Met Asp Phe Phe Asn
                85                  90                  95

Asp Asn Ile Met His Lys Gly Gly Lys Tyr Ile His Pro Lys Gly Gly
            100                 105                 110

Ser Pro Asn Pro Pro Asn Asn Thr Glu Thr Val Ile His Gly Asp Lys
            115                 120                 125

His Ala Ala Met Glu Phe Ile Phe Val Ser Pro Lys Asn Lys Asp Lys
            130                 135                 140

Arg Val Leu Val Tyr Ala His His His His His His His
145                 150                 155

<210> SEQ ID NO 2
<211> LENGTH: 160
<212> TYPE: PRT
<213> ORGANISM: Artificial Sequence
<220> FEATURE:
<223> OTHER INFORMATION: RussiaSea-002

<400> SEQUENCE: 2

Met Thr Thr Phe Leu Ile Lys His Lys Ala Ser Gly Lys Tyr Phe His
1               5                   10                  15

Pro Lys Gly Gly Thr Ser Asn Pro Pro Asn Gly Thr Asn Leu Val Leu
            20                  25                  30

His Ser Asp Ile His Glu Arg Met Tyr Phe Gln Phe Glu Val Val Asn
            35                  40                  45

Glu Arg Trp Arg Tyr Ile Lys His Val Ala Ser Glu Lys Ile Val His
        50                  55                  60

Pro Phe Gly Gly Lys Ala Asp Pro Leu Asn Gly Thr Asn Met Val Leu
65                  70                  75                  80

His Gln Asp Arg His Asp Arg Ala Leu Phe Ala Met Asp Phe Phe Asn
                85                  90                  95

Asp Asn Ile Arg His Lys Gly Gly Lys Tyr Ile His Pro Lys Gly Gly
            100                 105                 110

Ser Lys Asn Pro Ser Asn Gly Asn Leu Thr Val Met His Gly Asp Glu
            115                 120                 125

His Gly Ala Met Glu Phe Ile Phe Val Ser Pro Lys Asn Lys Asp Lys
            130                 135                 140

Arg Val Leu Val Tyr Ala Leu Glu His His His His His His His
145                 150                 155                 160
```

DIAGNOSTIC KITS AND METHODS CONFIGURED TO RAPIDLY AND NON-INVASIVELY DETERMINE PHYSIOLOGIC LEVELS OF GALACTOSE-DEFICIENT IgA1 (Gd-IgA1) IN THE SUBJECT OF IgA NEPHROPATHY

CROSS-REFERENCE TO RELATED APPLICATIONS

This application claims priority in U.S. Provisional Patent Application No. 62/927,281, filed Oct. 29, 2019, which is incorporated by reference in its entirety herein.

FIELD OF THE INVENTION

This disclosure relates to a lectin from *Crenomytilus grayanus* or *Mytilus trossulus*. Particularly, the invention relates to a reagent and method for detecting galactose-deficient IgA1 (Gd-IgA1), a reagent and method for diagnosing IgA nephropathy (IgAN) in a subject. The lectin from *Crenomytilus grayanus* or *Mytilus trossulus* can be used to evaluate the levels of Gd-IgA1 to non-invasively determine IgAN.

BACKGROUND OF THE INVENTION

IgA nephropathy cases account for the majority lesion found to cause primary glomerulonephritis throughout most developed countries of the world. Until now, an overall incidence of IgAN is about at least 2.5 per 100,000 individuals. Of such IgA nephropathy cases, 15 to 30% having a poor prognosis progress into renal failure, and there is no radical therapy because the etiology of IgA nephropathy is still unknown.

IgA nephropathy (IgAN), also known as Berger's disease, is a type of chronic glomerulonephritis characterized by IgA deposition dominantly in the glomerular mesangium area of the kidney. IgAN is a silent disease that may go unseen for years. It can happen at any age, but symptoms most often start before the age of 40. The most common symptom is blood in the urine (hematuria). It takes many years to progress to the stage where it causes problems. These include swelling, recurrent upper respiratory infections, or intestinal disease.

Further, people with IgA nephropathy may also have flank pain and a low fever. Very rarely, blood pressure can become dangerously high. The renal function declines faster in patients with comorbid proteinuria, hypertension, and renal insufficiency at the onset of the disease.

IgAN is the main causes of chronic kidney failure and uremia in young person. Clinically, IgAN patients only have mild proteinuria and hematuria which are not specific to IgAN. The studies have reported that the abnormal glycosylation in the hinge region (HR) of IgA1 is associated with the pathogenesis of IgAN. The definitive diagnosis of IgAN is a heavy burden on patients because it is based on a method involving biopsy in which a portion of the kidney is excised and immunologically stained to confirm IgA immune complex deposition in the mesangium.

Accordingly, it is very important how to develop a method for detecting presumed IgA nephropathy with a high accuracy, and the method being simply and quickly practicable without physical burden on subjects.

SUMMARY OF THE INVENTION

In view of the above-mentioned problem, the present invention provides a non-invasive diagnostic kit or/and a non-invasive diagnostic method for rapid diagnosing of IgAN patients.

In one embodiment, a kit for non-invasively detecting galactose-deficiency in IgA1 (Gd-IgA1), comprising a lectin provided from or originated from *Crenomytilus grayanus*.

In one embodiment, the lectin is RussiaSea-001 (*Crenomytilus grayanus* lectin/CGL).

In one embodiment, a kit for non-invasively detecting galactose-deficiency in IgA1 (Gd-IgA1), comprising a lectin provided from or originated from *Mytilus trossulus*.

In one embodiment, the lectin is RussiaSea-002 (*Mytilus trossulus* lectin/MTL).

BRIEF DESCRIPTION OF THE DRAWINGS

(FIG. 2C) were coated with 96-well microplates, respectively for ELISA-based analysis by measuring optical density (OD) value at 450 nm or fluorescence (Cy5). The results show that anti-human IgA1 antibodies could not recognize I-IgA1, Sd-IgA1, and Gd-IgA1. Histag-labeled RussiaSea-001 was bound to plausible Gd-IgA1 predominantly, but not so much to Sd-IgA1.

DETAILED DESCRIPTION OF THE INVENTION

Figure 1A:
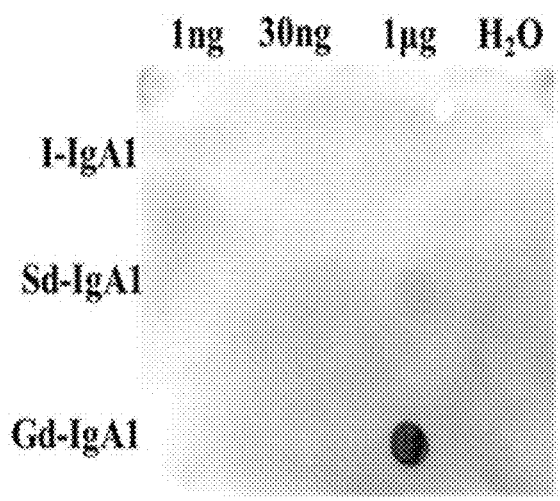
FIG. 1A shows that RussiaSea-001 had a higher binding capacity to Gd-IgA1 by dot blot analysis. 1 µg or more of Gd-IgA1 was detected by RussiaSea-001 (CGL), but intact IgA1 (I-IgA1) and desialylated-IgA1 (Sd-IgA1) both were undetectable.

The present invention provided is a lectin isolated from the sea mussels herein. Optionally, the lectin of the present invention is isolated from *Crenomytilus grayanus* or *Mytilus trossulus*.

In one embodiment, the lectin of the invention is selected from RussiaSea-001 (is also called CGL) isolated form *Crenomytilus grayanus*. Optionally, the lectin of the invention is selected from RussiaSea-002 (is also called MTL) isolated form *Mytilus trossulus*.

The lectin, RussiaSea-001 or RussiaSea-002, can bind specific sugars. The lectin of the invention is a dimer composed of a stable β-chain structure, and has three sites that bind sugars on each monomer. The lectin of the invention can be combined with galactose (Gal), N-acetylgalactosamine (GalNAc), and globular trisaccharides, and is classified as a family of galactose-binding lectin.

The lectin of the invention, RussiaSea-001 or RussiaSea-002, has a very high affinity to mucin-type glycoprotein, that characterized by the high content of the 0-glycoside-bound chains, preferably has a high affinity to N-acetyl-2-deoxy-2-amino-galactose (GalNAc/Gal), particularly specifically binds to Galactose-deficient IgA1 (Gd-IgA1). Therefore, the lectin of the invention can be used to develop an novel IgA1 galactose-deficient O-glycosylation assay for detecting the existence of Gd-IgA1 to determine a subject who is suffered from IgA nephropathy (IgAN) or not.

Further, the present invention also provided a diagnostic kit for detection of Gd-IgA1 in IgAN patients. The diagnostic kit can diagnose IgAN in a non-invasive manner using Enzyme-linked immunosorbent assay (ELBA), affinity chromatography column purification method, or modified test tube binding analysis, etc.

Optionally, RussiaSea-001 or RussiaSea-002 may be used to determine IgAN patients by ELISA-based binding assay. For example, RussiaSea-001 or RussiaSea-002 is labeled with a tag, including, but is not limited to, biotin, His tag, fluorescent substance (Cy3 or Cy5), or Digoxigenin (Dig). The tag-labeled lectin is mixed with a sample, and then the amount of Gd-IgA1 in the samples is analyzed by detecting an absorbance value or fluorescence intensity to determine a subject who is suffered from IgAN or not.

Optionally, an affinity chromatography column may be developed to determine IgAN patients. RussiaSea-001 or RussiaSea-002 is combined with chromatography resins, and then assembled into an affinity chromatography column. The chromatography resin can be a commercial resin, such as CNBr-activated Sepharose™, and AminoLink™Plus Coupling Resin/AminoLink™Plus. Samples are added into the affinity chromatography column, washed and then eluted. The eluted solution is collected for Western blot analysis and quantitative analysis.

Optionally, a test tube binding analysis is used to determine IgAN patients. A sample is added into a test tube and completely incubated with anti-IgA antibodies. Then, the lectin (RussiaSea-001 or RussiaSea-002) labeled with a tag is added. After washing and color reaction, the levels of Gd-IgA1 are determined by Western blot analysis or ELISA assay. As used herein, the term "tag" includes, but is not limited to, biotin, His tag, fluorescent substance (Cy3 or Cy5), or Digoxigenin (Dig).

In one embodiment, RussiaSea-001 can be obtained by homogenization of *Crenomytilus grayanus* and then passing through Sepharose 6B affinity column and Sephacryl S-200 gel filtration chromatography column. Optionally, the RussiaSea-001 also can be produced by genetic engineering. A sequence coding CGL with His-tag is cloned into pET21a(+) vector, and then transformed into competent cells to express RussiaSea-001 in bacteria. In addition, RussiaSea-002 can be obtained by homogenization of *Mytilus trossulus* and then passing through Sephacryl S-200 gel filtration chromatography column. Optionally, the RussiaSea-002 also can be obtained by cloning of MTL gene with His-tag into pET-40b (+) expression vector, and then transformed into competent cells to express RussiaSea-002 in bacteria.

Sequences of His-tagged RussiaSea-001 (artificial RussiaSea-001) (SEQ ID NO: 1) which can be employed in accordance with the invention are shown hereinbelow:

```
SEQ ID NO: 1:
MTTFLIKHKASGKFLHPYGGSSNPANNTKLVLHSDIHERMYFQFDVVDER

WGYIKHVASGKIVHPYGGQANPPNETNMVLHQDRHDRALFAMDFFNDNIM

HKGGKYIHPKGGSPNPPNNTETVIHGDKHAAMEFIFVSPKNKDKRVLVYA

HHHHHHHH
```

Sequences of His-tagged RussiaSea-002 (artificial RussiaSea-002) (SEQ ID NO: 2) which can be employed in accordance with the invention are shown hereinbelow:

```
SEQ ID NO: 2:
MTTFLIKHKASGKYFHPKGGTSNPPNGTNLVLHSDIHERMYFQFEVVNER

WRYIKHVASEKIVHPFGGKADPLNGTNMVLHQDRHDRALFAMDFFNDNIR

HKGGKYIHPKGGSKNPSNGNLTVMHGDEHGAMEFIFVSPKNKDKRVLVYA

LEHHHHHHHH
```

Further, the present invention provided a method for detecting Gd-IgA1, comprising the steps of (1) providing a sample; (2) providing a diagnostic kit of the invention; and (3) treating the sample with the diagnostic kit resulting in the specific binding of lectin and Gd-IgA1.

As used herein a biological sample is a sample derived from a subject and includes, but is not limited to, any cell, tissue or biological fluid. For example, the sample can be a tissue biopsy, blood or serum, and the like. The lectin of the invention can be used to determine the existence of Gd-IgA1 in sera because the lectin of the invention is capable of specifically binding to Gd-IgA1. If the level of Gd-IgA1 in the serum collected from a subject is higher than a specific value, the subject may be indicated as an IgAN patient. If the level of Gd-IgA1 in the serum collected from a subject is lower than a specific value, the subject is not an IgAN patient.

In summary, the present invention provides a novel rapid, effective and high-specificity method for non-invasively detecting Gd-IgA1 developed by RussiaSea-001 or RussiaSea-002. The RussiaSea-001 or RussiaSea-002 of the present invention has huge potential for developing a rapid screening reagent or lateral flow immunochromatography (IFLA) test paper for commercial use. In other word, the present invention provides a novel diagnostic method for improving or replacing the invasive surgery acquiring the renal tissue sections to detect IgAN.

Additional specific embodiments of the present invention include, but are not limited to the following:

Example 1

RussiaSea-001 Binding Assay Using Enzymatically Generated Cd-IgA1

The present invention provides a method preparing intact-IgA1 (I-IgA1) treated with neuraminidase to produce desaliyic acid IgA1 (Sd-IgA1), and further preparing intact-IgA1 (I-IgA1) treated with β-galactosidase to produce galactose-deficient IgA1 (Gd-IgA1). In dot blot analysis, the variety types of constant concentration IgA1s were transferred onto a PVDF membrane, dried, incubated with RussiaSea-001, and then detected by anti-His antibodies. Similarly, in Western blotting analysis, the variety types of generated IgA1 were loaded on SDS-PAGE, incubated with RussiaSea-001, and detected by anti-His antibodies. In addition, anti-IgA1 antibodies were coated on ELISA plates, and incubated with sera from healthy control (HC) subjects, IgA nephropathy (IgAN) patients, and lupus nephritis (LN) patients, respectively. Biotin- or fluorescent-labeled RussiaSea-001 was added to produce color directly or by adding a substrate to determine the binding ability of RussiaSea-001 and Gd-IgA1.

Referring to FIG. 1A, RussiaSea-001 has a higher binding capacity to Gd-IgA1. 1 μg or more of Gd-IgA1 was detected by RussiaSea-001, and intact-IgA1 (I-IgA1) and Sd-IgA1 both were undetectable according to the results of dot blot analysis.

Figure 1B:
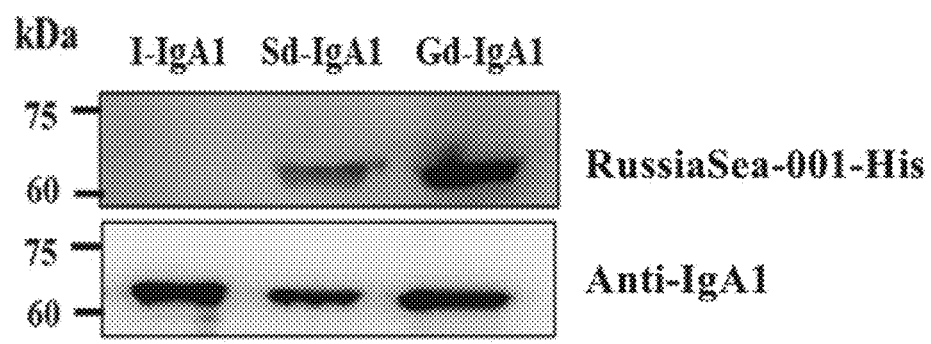
FIG. 1B shows that RussiaSea-001 was bound to plausible Gd-IgA1 predominantly by Western blot analysis. Compared with intact IgA1 and Sd-IgA1, RussiaSea-001 was most significantly capable of binding Gd-IgA1.

Referring to FIG. 1B, the binding of RussiaSea-001 and Gd-IgA1 was significant compared with I-IgA1 and Sd-IgA1, respectively according to the results of Western blot analysis.

Figure 2A:
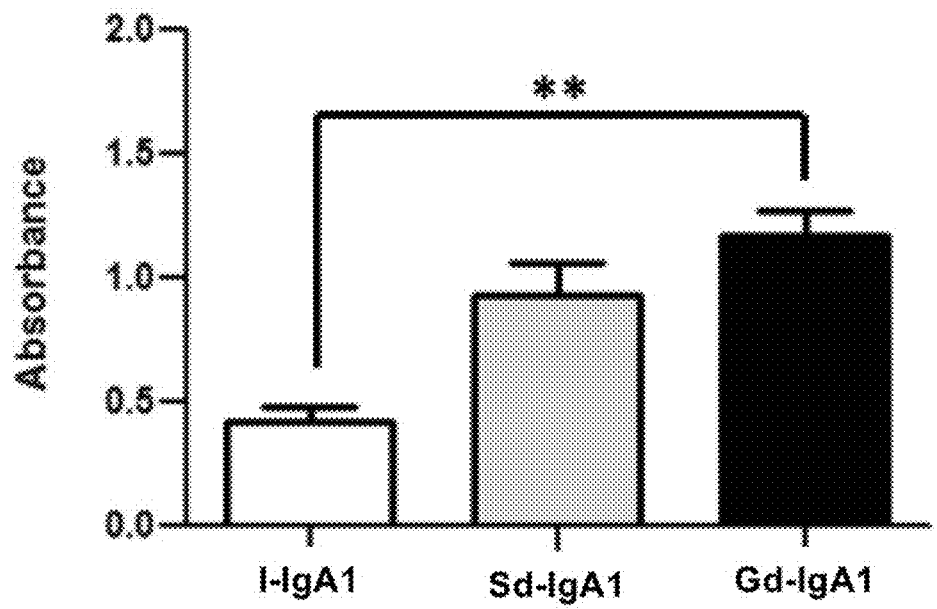
FIGS. 2A to 2C show that the anti-human IgA1 antibody (FIGS. 2A to 2B) and Histag-labeled RussiaSea-001.
Figure 2B:
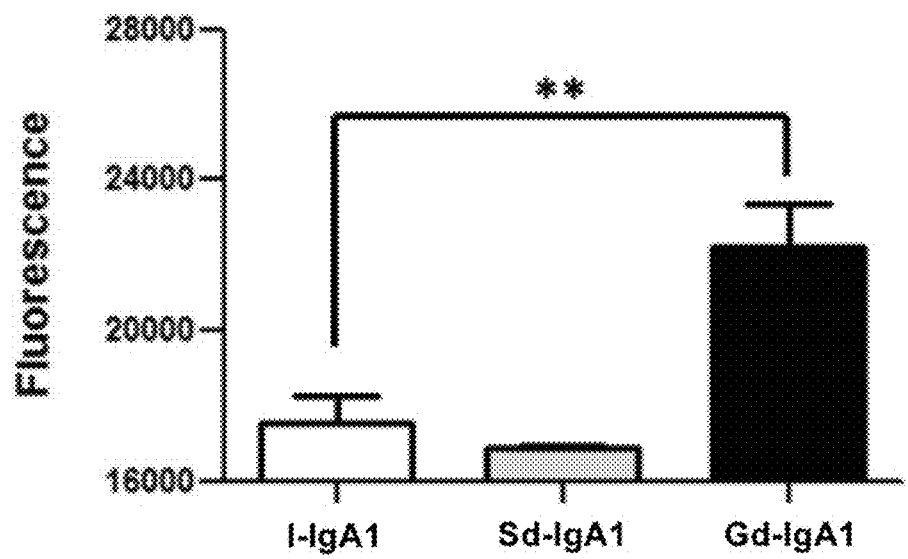
Figure 2C:
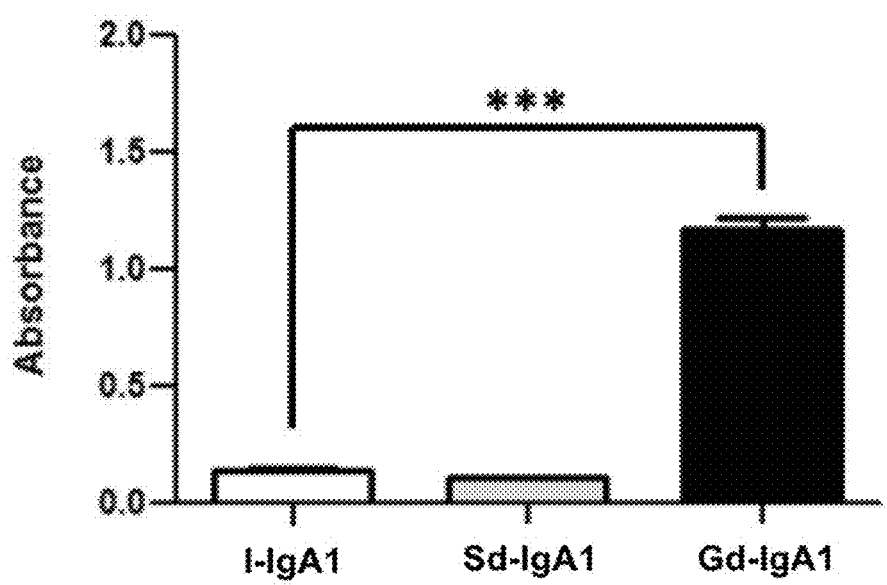

Referring to FIGS. 2A to 2C, 96-well microplates were coated with anti-human IgA1 antibodies (FIGS. 2A-2B) and His-Tagged RussiaSea-001 (FIG. 2C), respectively, and then I-IgA1, Sd-IgA1, or Gd-IgA1 were added into the wells of the 96-well microplates for ELISA assay by measuring optical density (OD) value at 450 nm or fluorescence. The results show that anti-human IgA1 antibodies could not recognize I-IgA1, Sd-IgA1, and Gd-IgA1 (FIGS. 2A-2B). The lectin (His-tagged RussiaSea-001) was bound to Gd-IgA1 predominantly (FIG. 2C), but not so much to Sd-IgA1.

Example 2

RussiaSea-001 Binding Assay to Detect Sera from IgAN Patients

The sera collected from 10 healthy control (HC) subjects and 10 IgAN patients were analyzed by the RussiaSea-001 binding assay (ELISA assay). The anti-IgA1 antibodies were coated onto ELISA plates and incubated with sera of HC subjects or IgAN patients. Biotin-labeled RussiaSea-001 was added to produce color or light for determining the binding capability of RussiaSea-001 for Gd-IgA1. In addition, the binding capability between RussiaSea-001 and Gd-IgA1 in sera from HC subjects, IgAN patients, and lupus nephritis (LN) patients, respectively was analyzed.

Figure 3:
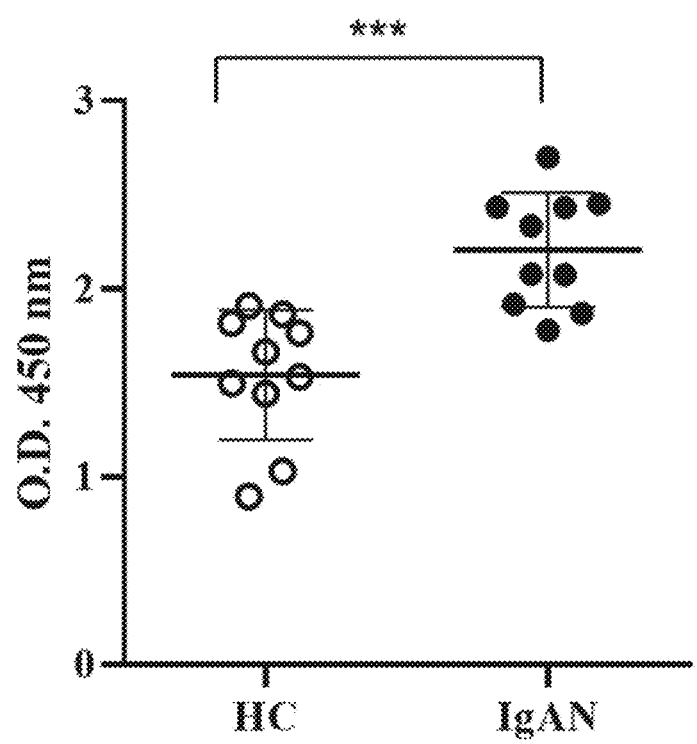
FIG. 3 shows results of ELISA assay. RussiaSea-001 was specifically bound to Gd-IgA1 in sera from IgAN patients.
Figure 4:
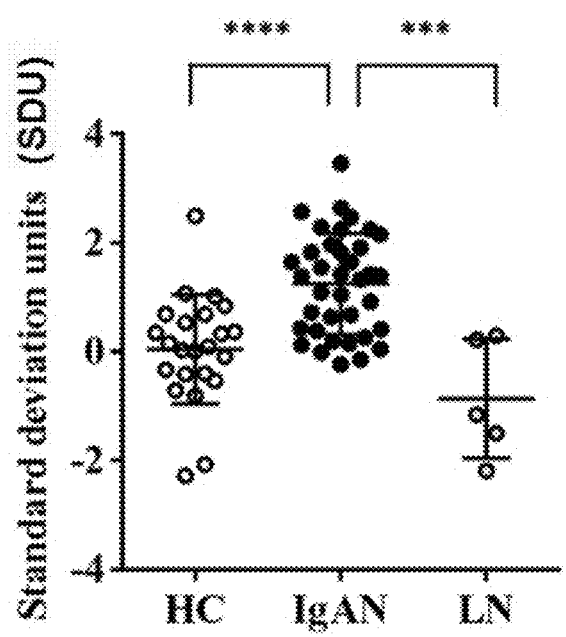
FIG. 4 shows results of ELISA assay. RussiaSea-001 was specifically bound to Gd-IgA1 in sera from IgAN patients, compared with IgA1 in sear from healthy control (HC) subjects and IgAN patients. The levels of Gd-IgA1 in sera from IgAN patients were more significantly increased than those of HC subjects and lupus nephritis (LN) patients.

Referring to FIG. 3, RussiaSea-001 was specifically bound to Gd-IgA1 in sera from IgAN patients. As shown in FIG. 4, RussiaSea-001 was specifically bound to Gd-IgA1 in sera from IgAN patients, compared with IgA1 in sera from HC subjects or IgAN patients. The levels of Gd-IgA1 in sera from IgAN patients were significantly increased, compared with BC subjects and LN patients.

Example 3

Purification of Gd-IgA1 by Combined Affinity Chromatography Column

Figure 5:
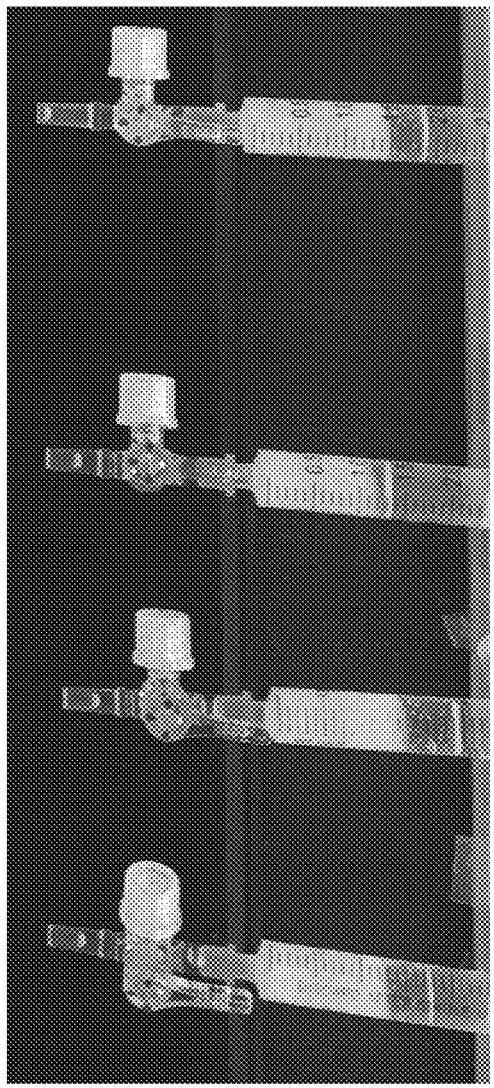
FIG. 5 shows schematic illustration of the RussiaSea-001 affinity chromatography column.

An affinity chromatography column was developed by asset bling CNBr-activated Sepharose 4B and RussiaSea-001 via cyanogen bromide method. The schematic illustration of the RussiaSea-001 affinity chromatography column was shown in FIG. 5.

Sera from healthy control (BC) subjects, IgAN patients, and lupus nephritis (LN) patients were respectively passed through RussiaSea-001 affinity chromatography, and then washed with glycine solution to elute Gd-IgA1 from resins. The levels of Gd-IgA1 in elution solution were determined by Western blot analysis. SDS-PAGE was performed on different types of IgA1, and then incubated with anti-Gd-IgA1 antibodies (KMS antibody) or anti-IgA1 antibodies. Incubation of the enzyme-conjugated secondary antibodies with appropriate substrates would produce color or light for detection of the levels of Gd-IgA1 and IgA1, respectively. The results were expressed as a ratio of Gd-IgA1/IgA1. In addition, RussiaSea-001 binding assay in sera from BC subjects and IgAN patients respectively was conducted to detect the levels of Gd-IgA1 in sera, as shown in standard deviation units (SDU). SDU of each sample=(sample absorbance mean absorbance of healthy controls)/standard deviation of healthy controls, wherein the mean and SD values of HC calculated in each experiment were used.

Figure 6:
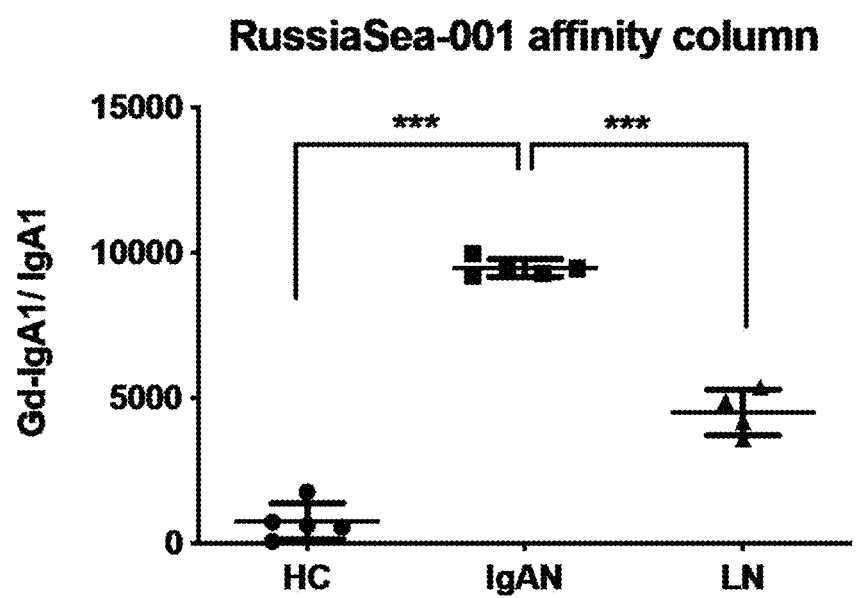
FIG. 6 shows increased Gd-IgA1 protein levels after enriched with RussiaSea-001 affinity column, in IgAN patients, compared with those of HC subjects and LN patients. RussiaSea-001 affinity column could specifically purify Gd-IgA1 in sera.

FIG. 6 shows the change of Gd-IgA1/IgA1 ratio after sera flowing through RussiaSea-001 affinity column. Gd-IgA1 protein levels in IgAN patients were increased, compared with those of HC subjects and LN patients RussiaSea-001 affinity column could specifically purify Gd-IgA1 in sera.

Example 4

Modified Tube Method with RussiaSea-001 in Serum Sample from IgAN Patients

Figure 7:
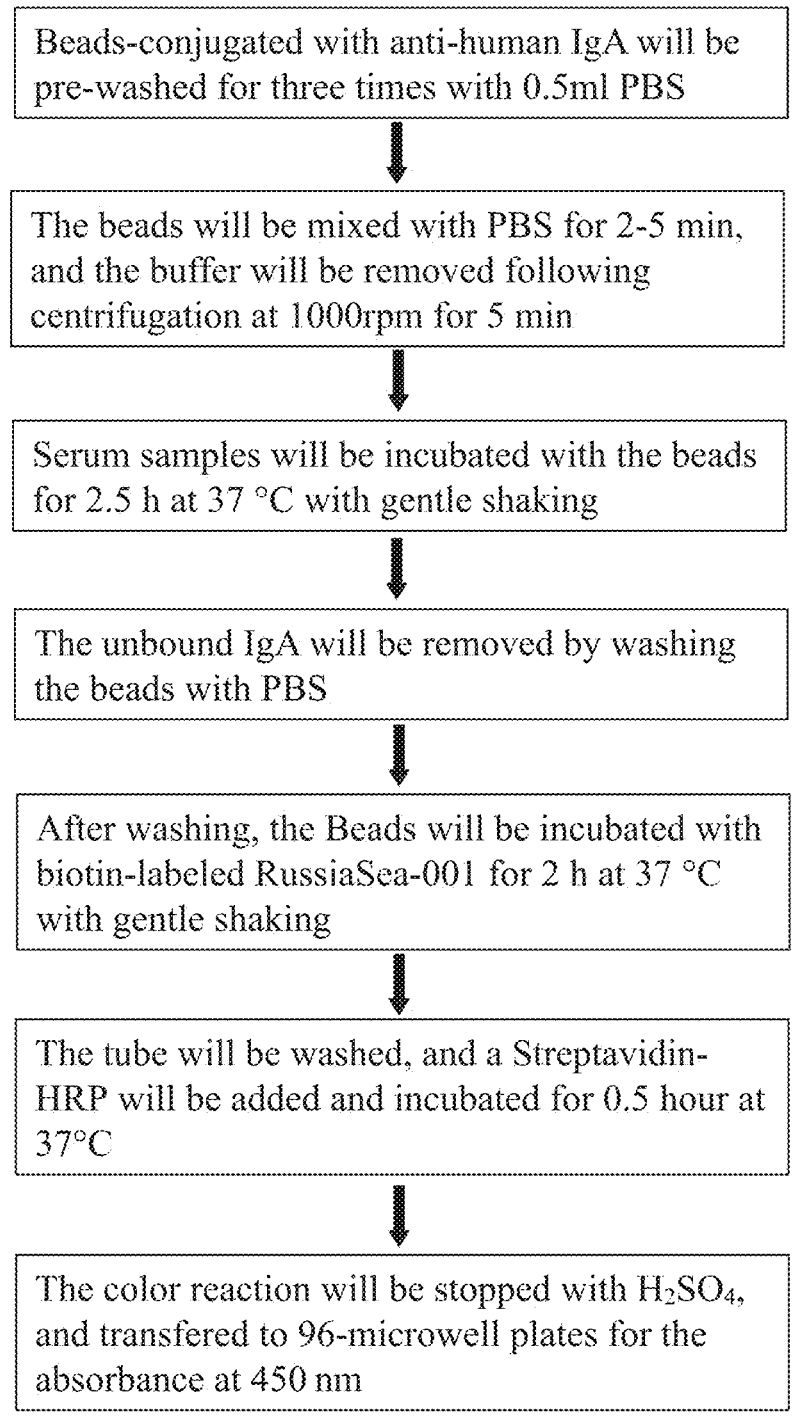
FIG. 7 is a flow chart to represent operating steps of the modified tube method according to another embodiment of the present invention.

The schematic representation of the modified tube method was used for isolation of IgA1 in sera and then recognizing Gd-IgA1 in sera of FIC subjects, or IgAN patients, or LN patients by RussiaSea-001. The steps of purification and analysis were shown in FIG. 7 and as follow.

Beads-conjugated with anti-human IgA (Thermo Scientific) will be pre-washed for three times with 0.5 ml PBS (1× Phosphate Buffered Saline; pH7.4). The beads will be mixed with PBS for 2-5 min, and the buffer will be removed following centrifugation at 1000 rpm for 5 min. Serum samples will be incubated with the beads for 2.5 h at 37° C. with gentle shaking. The unbound IgA will be removed by washing the beads with PBS for ten times. After washing, the Beads will be incubated with biotin-labeled RussiaSea-001 for 2 h at 37° C. with gentle shaking. The tube will be washed, and a Streptavidin-HRP will be added and incubated for 0.5 hour at 37° C. The color reaction will be stopped with $H_2SO_4$, and transfered to 96-microwell plates for the absorbance at 450 nm via an ELISA reader. The results represent by the ratio of Gd-IgA1/IgA1/IgA1.

Figure 8:
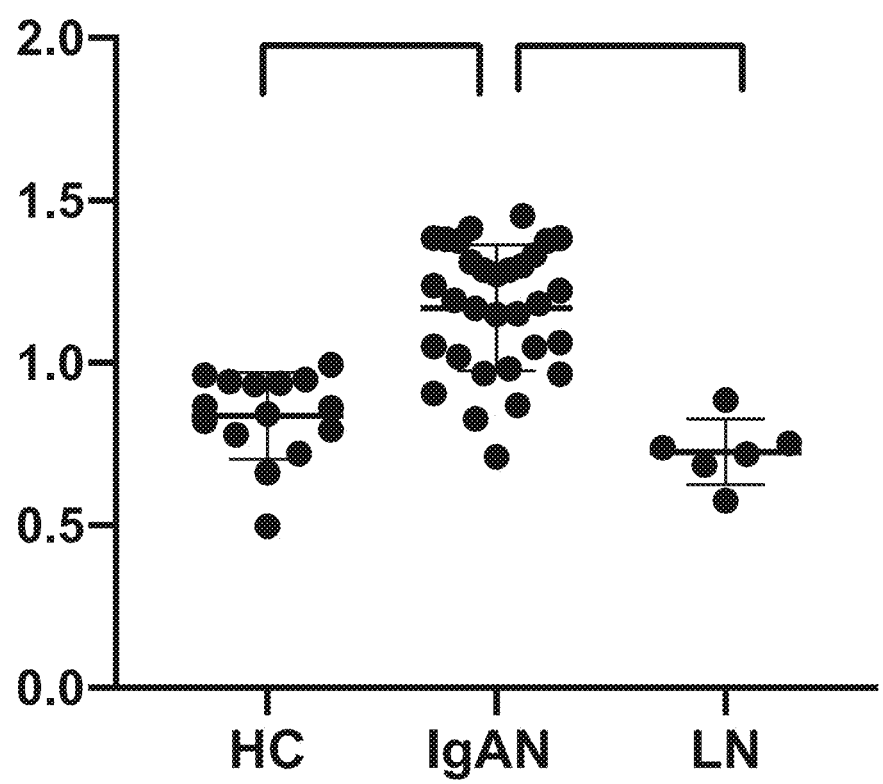
FIG. 8 shows that Gd-IgA1 levels in IgAN patients were significantly increased, compared with HC subjects or LN patients after treatment of modified tube method with RussiaSea-001. Gd-IgA1 levels were determined by measuring the absorbance of Biotin-labeled RussiaSea-001.

Referring to FIG. 8, Gd-IgA1 levels in IgAN patients were significantly increased, compared with HC subjects and LN patients after treatment of modified tube method with RussiaSea-001.

Figure 9:
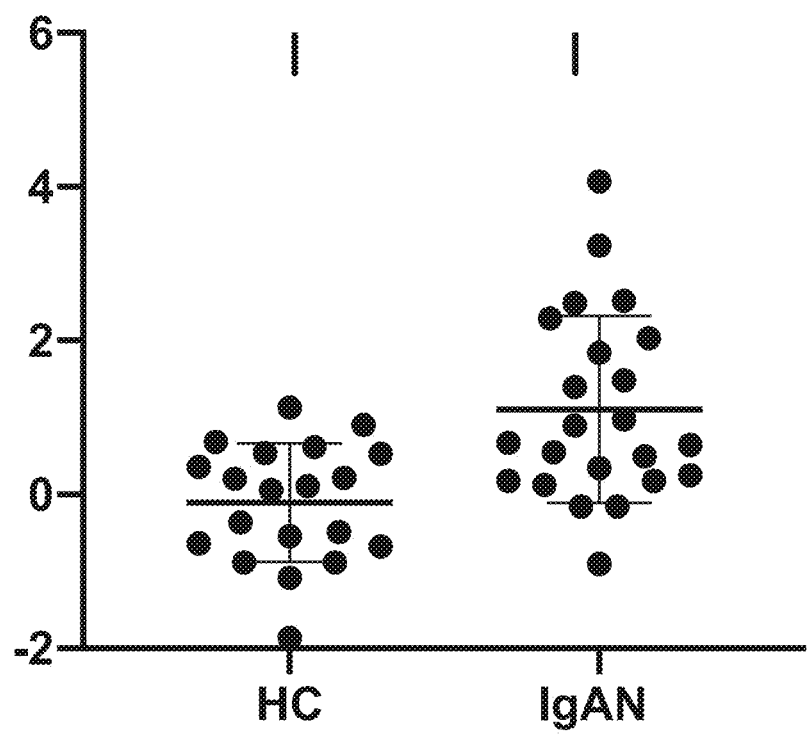
FIG. 9 shows that the results of sera were purified by RussiaSea-001 test tube and then analyzed with ELISA assay.

Sera were purified by RussiaSea-001 test tube and then analyzed with ELISA assay by measuring the value of optical density (OD) at 450 nm. Referring to FIG. 9, the levels of Gd-IgA1 significantly increased in serum of IgAN patients, compared to those of HC subjects and LN patients, respectively. In other words, the present invention provides and proves Gd-IgA1 in sera specifically purified by Russia-Sea-001modified tube method.

Example 5

RussiaSea-002 Binding Assay Using Enzymatically Generated Gd-IgA1

The present invention provides another method preparing intact-IgA1 (I-IgA1) treated with neuraminidase to produce desaliyic acid IgA (Sd-IgA1), and further preparing intact-IgA1 (I-IgA1) treated with β-galactosidase to produce galactose-deficient IgA1 (Gd-IgA1). In dot blot analysis, the variety types of constant concentration IgA1s were transferred onto a PVDF membrane, dried, incubated with RussiaSea-002, and then detected by anti-His antibodies. Similarly, in Western blotting analysis, the variety types of generated IgA1 were loaded on SDS-PAGE, incubated with RussiaSea-002, and detected by anti-His antibodies. In addition, anti-IgA1 antibodies were coated on ELISA plates, and incubated with sera from healthy control (HC) subjects, IgA nephropathy (IgAN) patients, and lupus nephritis (LN) patients, respectively. Biotin- or fluorescent-labeled Russia-Sea-002 was added to produce color directly or by adding a substrate to determine the binding ability of RussiaSea-002 and Gd-IgA1

Figure 10:
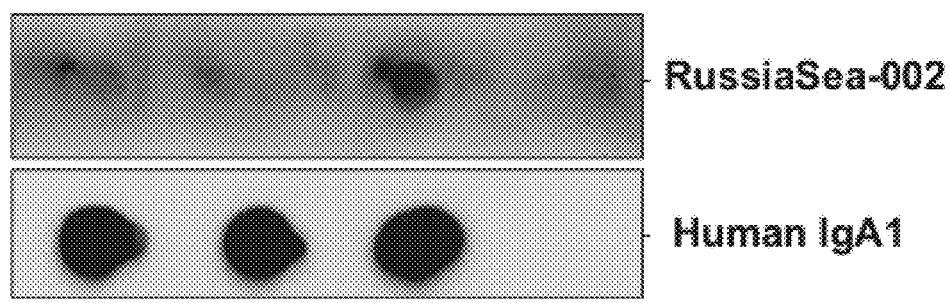
FIG. 10 shows results of dot blot analysis. RussiaSea-002 was bound to Gd-IgA1, but not bound to I-IgA1 or Sd-IgA1.

In one embodiment, FIG. 10 shows results of dot blot analysis. RussiaSea-002 could bind to Gd-IgA1, however not bind to or Sd-IgA1. In contrast, human anti-IgA antibodies could not bind to all of IgA1. That is to say human anti-IgA antibodies could not bind I-IgA1, Sd-IgA1, and Gd-IgA1.

Figure 11A:
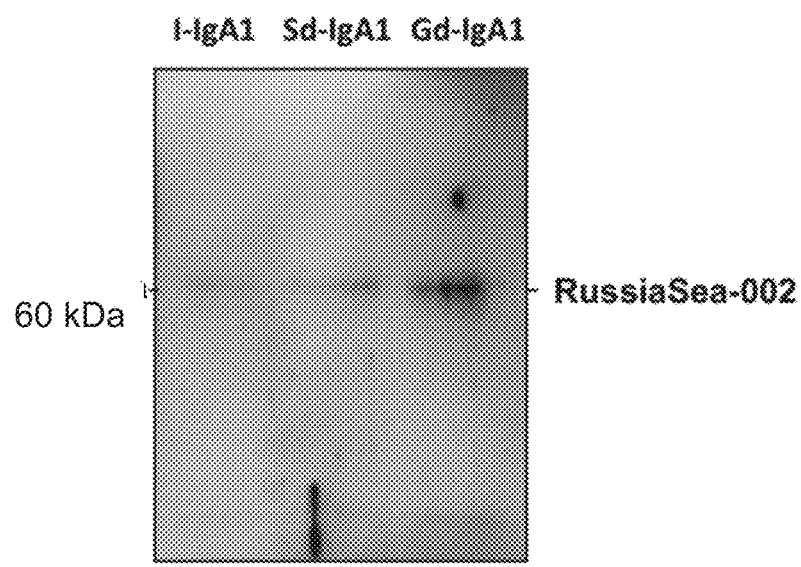
FIGS. 11A-11B show results of Western blot analysis. The binding ability of RussiaSea-002 (MTL) and Gd-IgA1 was significant, compared with I-IgA1 and Sd-IgA1.
Figure 11B:
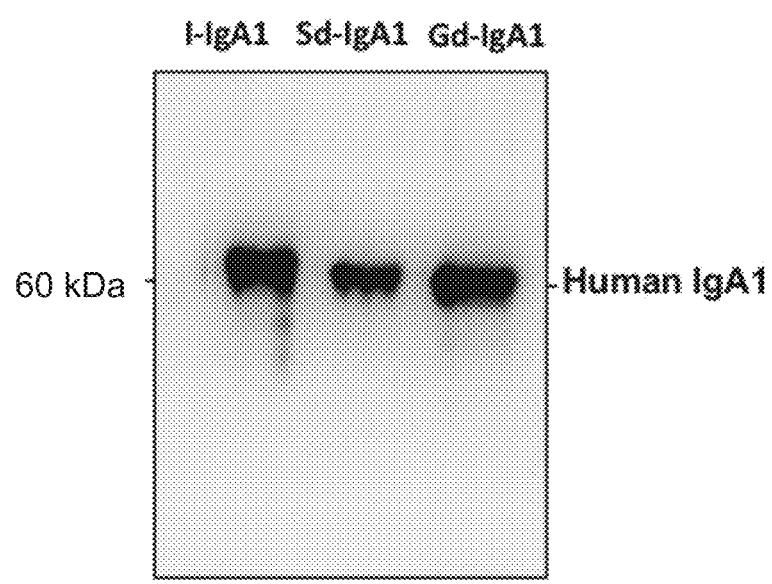

Further, FIGS. 11A-11B show that the binding capability of RussiaSea-002 to Gd-IgA1 was more significant than or Sd-IgA1 via Western blot analysis.

Figure 12:
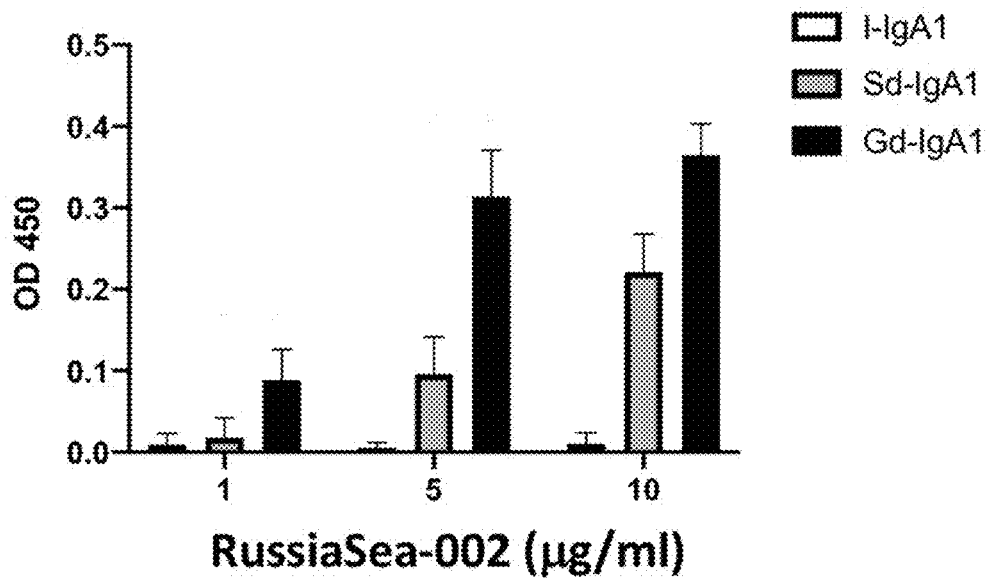
FIG. 12 shows results of ELISA binding assay. 1-10 µg/ml of Biotin-labeled RussiaSea-002 was bound to Gd-IgA1 only, and not bound to I-IgA1 or Sd-IgA1.

Moreover, FIG. 12 shows the results of ELISA assay using Biotin-labeled RussiaSea-002. Biotin-labeled Russia-Sea-002 was bound to Gd-IgA1 only, in contrast, not bound to I-IgA1 and Sd-IgA1 respectively.

The results show that the highest level of binding capability with RussiaSea-002 was observed in Gd-IgA1, followed by the mild degree of Sd-IgA1, but very little binding with I-IgA1.

Example 6

ELISA-Based Analysis Using RussiaSea-002 to Detect Sera from IgAN Patient

Sera were collected from 16 HC subjects and 15 IgAN patients. The anti-IgA1 antibodies were coated onto ELISA plates and incubated with sera of HC subjects or IgAN patients. Biotin-labeled RussiaSea-002 was added to ELISA plates to produce color or light by enzyme-substrate reaction for determining the binding capability of RussiaSea-002 for Gd-IgA1 by measuring the value of optical density (OD) at 450 nm. In addition, the binding capability between RussiaSea-002 and Gd-IgA1 in sera from HC subject, IgAN patients, and lupus nephritis (LN) patients, respectively was analyzed.

Figure 13:
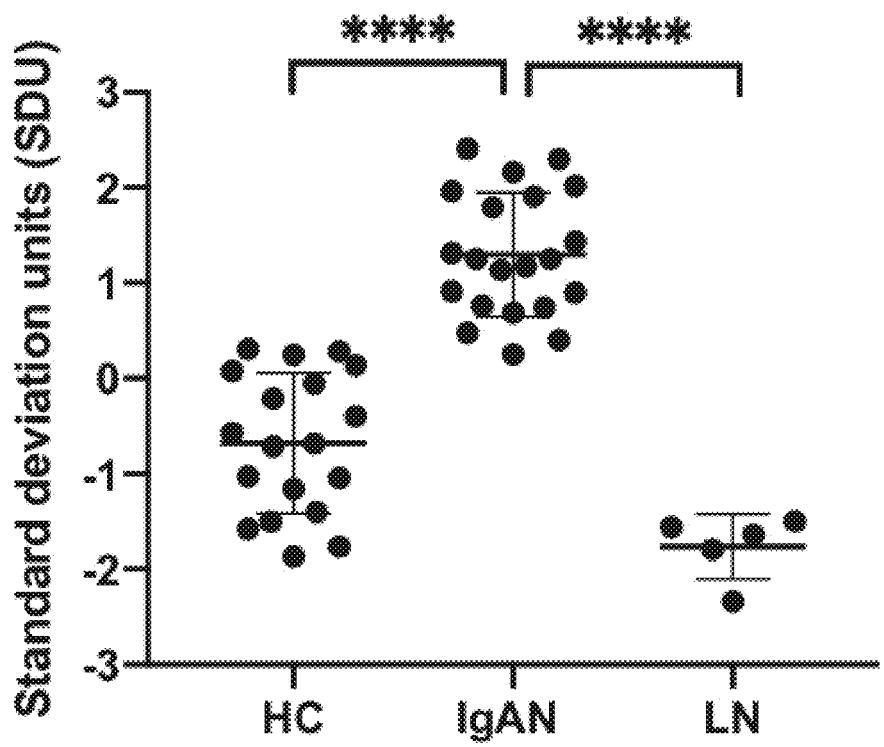
FIG. 13 shows that Biotin-labeled RussiaSea-002 was specifically bound to Gd-IgAN in sera from IgAN patients, and Gd-IgA1 protein levels in sera from IgAN patients were higher than those of HC subjects or LN patients.

Referring to FIG. 13, the data show that Biotin-labeled RussiaSea-002 was specifically bound to Gd-IgA1 in sera from IgAN patients. Compared with IgA1 in sera from FTC subjects or LN patients, Biotin-labeled RussiaSea-002 more specifically bound to Gd-IgA1 in sera from IgAN patients. In other words, the Gd-IgA1 protein levels in IgAN patients were significantly increased, compared with those of HC subjects and LN patients, respectively.

All examples provided herein are intended for pedagogical purposes of aiding the reader in understanding the invention and the concepts contributed by the inventors to further the art, and are not to be construed as limitations to such specifically recited examples and conditions, nor does the organization of such examples in the specification relate to a showing of the superiority or inferiority of the invention. Although one or more embodiments of the present invention have been described in detail, it should be understood that the various changes, substitutions, and alterations could be made hereto without departing from the spirit and scope of the invention.

It is intended that the specification and examples be considered as examples only, with a true scope and spirit of the invention being indicated by the following claims.

What is claimed is:

1. A method for detecting galactose-deficient IgA1 (Gd-IgA1), comprising
   (a) providing a sample from a subject,
   (b) providing a kit of diagnosing galactose-deficient IgA1 (Gd-IgA1), comprising a lectin from *Crenomytilus grayanus*, wherein the lectin is RussiaSea-001 (*Crenomytilus grayanus* lectin/CGL), wherein the RussiaSea-001 is SEQ ID NO: 1, wherein the SEQ ID NO: 1 has a specificity to N-acetyl-2-deoxy-2-amino-galactose (GalNAc/Gal), wherein the kit is applied to diagnosing a subject with galactose-deficient IgA1, wherein the subject is selected from IgA nephropathy (IgAN) patient, and lupus nephritis (LN) patients, and
   (c) treating the sample with the kit resulting in the specific binding capability between lectin and Gd-IgA1.

2. The method of claim 1, wherein the sample is a serum.

3. A kit for diagnosing galactose-deficient IgA1 (Gd-IgA1), comprising a lectin isolated from *Mytilus trossulus*, wherein the lectin is RussiaSea-002 (*Mytilus trossulus* lectin/MTL), wherein the RussiaSea-002 is SEQ ID NO: 2, wherein the SEQ ID NO: 2 has a specificity to N-acetyl-2-deoxy-2-amino-galactose (GalNAc/Gal), wherein the kit is applied to diagnosing a subject with galactose-deficient IgA1, wherein the subject is selected from IgA nephropathy (IgAN) patient, and lupus nephritis (LN) patients.

4. The kit of claim 3, which is applied to enzyme-linked immunosorbent assay (ELISA), affinity chromatography column purification, or modified test tube binding analysis.

5. A method for detecting galactose-deficient IgA1 (Gd-IgA1), comprising:
   (a) providing a sample from a subject,
   (b) providing the kit of claim 3, and
   (c) treating the sample with the kit resulting in the specific binding capability between lectin and Gd-IgA1.

6. The method of claim 5, wherein the sample is a serum.

* * * * *